US010202323B2

(12) United States Patent
Parvulescu et al.

(10) Patent No.: US 10,202,323 B2
(45) Date of Patent: Feb. 12, 2019

(54) PROCESS FOR PREPARING AN ARYLPROPENE

(71) Applicant: BASF SE, Ludwigshafen (DE)

(72) Inventors: Andrei-Nicolae Parvulescu, Ruppertsberg (DE); Ulrich Müller, Neustadt (DE); Thomas Fenlon, Mannheim (DE); Sumana Chaturvedula, Frankfurt (DE); Stefan Rüdenauer, Weinheim (DE); Andreas Lanver, Mannheim (DE); Ralf Pelzer, Fürstenberg (DE); Klaus Ebel, Heddesheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/744,324

(22) PCT Filed: Jul. 15, 2016

(86) PCT No.: PCT/EP2016/066923
§ 371 (c)(1),
(2) Date: Jan. 12, 2018

(87) PCT Pub. No.: WO2017/009458
PCT Pub. Date: Jan. 19, 2017

(65) Prior Publication Data
US 2018/0208532 A1    Jul. 26, 2018

(30) Foreign Application Priority Data
Jul. 15, 2015    (EP) ..................... 15176820

(51) Int. Cl.
*C07C 41/18* (2006.01)
*B01J 29/86* (2006.01)
*B01J 29/70* (2006.01)

(52) U.S. Cl.
CPC ........... *C07C 41/18* (2013.01); *B01J 29/7007* (2013.01); *B01J 29/7038* (2013.01); *B01J 29/86* (2013.01)

(58) Field of Classification Search
CPC ....... C07C 41/18; B01J 29/86; B01J 29/7007; B01J 29/7038; B01J 29/70
See application file for complete search history.

(56) References Cited

U.S. PATENT DOCUMENTS

| | | | |
|---|---|---|---|
| 2,373,982 A | 4/1945 | Sturrock et al. | |
| 4,026,951 A | 5/1977 | Bauer et al. | |
| 4,456,582 A | 6/1984 | Marosi et al. | |
| 9,446,390 B2 | 9/2016 | Parvulescu et al. | |
| 9,540,305 B2 | 1/2017 | Parvulescu et al. | |
| 9,561,995 B2 | 2/2017 | Maurer et al. | |
| 9,688,648 B2 | 6/2017 | Teles et al. | |
| 9,695,099 B2 | 7/2017 | Liu et al. | |
| 9,725,428 B2 | 8/2017 | Teles et al. | |
| 9,738,616 B2 | 8/2017 | Riedel et al. | |
| 9,765,001 B2 | 9/2017 | Rüdenauer et al. | |
| 9,765,003 B2 | 9/2017 | Vautravers et al. | |
| 9,765,238 B2 | 9/2017 | Klopsch et al. | |
| 9,856,199 B2 | 1/2018 | Hickmann et al. | |
| 2015/0090226 A1 | 4/2015 | Dolan et al. | |
| 2015/0090231 A1 | 4/2015 | Dolan et al. | |
| 2015/0090344 A1 | 4/2015 | Dolan et al. | |
| 2015/0090610 A1 | 4/2015 | Dolan et al. | |
| 2015/0090611 A1 | 4/2015 | Dolan et al. | |
| 2015/0094202 A1 | 4/2015 | Dolan et al. | |
| 2016/0186932 A1 | 6/2016 | Weickert et al. | |
| 2016/0201853 A1 | 7/2016 | Weickert et al. | |
| 2016/0201854 A1 | 7/2016 | Weickert et al. | |
| 2016/0250624 A1 | 9/2016 | Parvulescu et al. | |
| 2016/0256859 A1 | 9/2016 | Parvulescu et al. | |
| 2016/0264543 A1 | 9/2016 | Vautravers et al. | |
| 2016/0279621 A1 | 9/2016 | Parvulescu et al. | |
| 2016/0325228 A1 | 11/2016 | Feyen et al. | |
| 2016/0332152 A1 | 11/2016 | Parvulescu et al. | |
| 2017/0037020 A1 | 2/2017 | Rüdenauer et al. | |
| 2017/0037021 A1 | 2/2017 | Stork et al. | |
| 2017/0037022 A1 | 2/2017 | Stork et al. | |
| 2017/0037296 A1 | 2/2017 | Kimura et al. | |
| 2017/0044421 A1 | 2/2017 | Parvulescu et al. | |
| 2017/0225959 A1 | 8/2017 | Maurer et al. | |
| 2017/0233780 A1 | 8/2017 | Breuer et al. | |
| 2017/0233874 A1 | 8/2017 | Aust et al. | |
| 2017/0246620 A1 | 8/2017 | Parvulescu et al. | |
| 2017/0275076 A1 | 9/2017 | Edgington et al. | |
| 2017/0275225 A1 | 9/2017 | Riedel et al. | |
| 2017/0283352 A1 | 10/2017 | Fenlon et al. | |
| 2017/0292084 A1 | 10/2017 | Stork et al. | |
| 2017/0298034 A1 | 10/2017 | Riedel et al. | |
| 2017/0334820 A1 | 11/2017 | Pelzer et al. | |
| 2017/0334824 A1 | 11/2017 | Pelzer et al. | |
| 2017/0336030 A1 | 11/2017 | Weickert et al. | |
| 2017/0355670 A1 | 12/2017 | Rüdenauer et al. | |
| 2017/0362532 A1 | 12/2017 | Pelzer | |
| 2018/0002266 A1 | 1/2018 | Bru Roig et al. | |
| 2018/0022611 A1 | 1/2018 | Feyen et al. | |

FOREIGN PATENT DOCUMENTS

| | | |
|---|---|---|
| CN | 102491884 A | 6/2012 |
| CN | 103058835 A | 4/2013 |
| DE | 2418974 B1 | 9/1975 |
| EP | 0007081 A1 | 1/1980 |
| GB | 1444897 A | 8/1976 |
| SU | 261380 | 1/1970 |
| SU | 355144 | 1/1972 |
| WO | WO-2013117536 A2 | 8/2013 |
| WO | WO-2013117537 A1 | 8/2013 |
| WO | WO-2014122152 A1 | 8/2014 |

(Continued)

OTHER PUBLICATIONS

U.S. Appl. No. 61/939,889.

(Continued)

*Primary Examiner* — Rosalynd A Keys
(74) *Attorney, Agent, or Firm* — Ashley I. Pezzner

(57) ABSTRACT

A process for preparing an arylpropene from a diarylpropane by gas phase thermolysis in the presence of boron containing zeolitic material comprising a membered ring (MR) pore system greater than 10 MR.

21 Claims, No Drawings

(56) References Cited

FOREIGN PATENT DOCUMENTS

| | | |
|---|---|---|
| WO | WO-2015018793 A1 | 2/2015 |
| WO | WO-2015018807 A2 | 2/2015 |
| WO | WO-2015018815 A1 | 2/2015 |
| WO | WO-2015025250 A1 | 2/2015 |
| WO | WO-2015025268 A1 | 2/2015 |
| WO | WO-2015032851 A2 | 3/2015 |
| WO | WO-2015059175 A1 | 4/2015 |
| WO | WO-2015083113 A1 | 6/2015 |
| WO | WO-2015107156 A2 | 7/2015 |
| WO | WO-2015123530 A1 | 8/2015 |
| WO | WO-2015123531 A1 | 8/2015 |
| WO | WO-2015169939 A1 | 11/2015 |
| WO | WO-2015185633 A1 | 12/2015 |
| WO | WO-2016024201 A1 | 2/2016 |
| WO | WO-2016066629 A1 | 5/2016 |
| WO | WO-2016074918 A1 | 5/2016 |
| WO | WO-2016075100 A1 | 5/2016 |
| WO | WO-2016075129 A1 | 5/2016 |
| WO | WO-2016/116406 A1 | 7/2016 |
| WO | WO-2016135133 A1 | 9/2016 |
| WO | WO-2016180807 A1 | 11/2016 |
| WO | WO-2016180809 A1 | 11/2016 |
| WO | WO-2017009205 A1 | 1/2017 |
| WO | WO-2017009462 A1 | 1/2017 |

OTHER PUBLICATIONS

U.S. Appl. No. 61/939,895.
U.S. Appl. No. 61/939,896.
U.S. Appl. No. 61/990,490.
U.S. Appl. No. 61/990,773.
U.S. Appl. No. 62/081,243.
U.S. Appl. No. 15/129,222, filed Sep. 26, 2016, Schwab.
U.S. Appl. No. 15/315,636, filed Dec. 1, 2016, Feyen.
U.S. Appl. No. 15/537,128, filed Jun. 16, 2017, Vautravers et al.
U.S. Appl. No. 15/550,581, filed Aug. 11, 2017, Riedel et al.
U.S. Appl. No. 15/555,723, filed Sep. 5, 2017, Rüdenauer et al.
U.S. Appl. No. 15/557,370, filed Sep. 11, 2017, Schrader et al.
U.S. Appl. No. 15/571,107, filed Nov. 1, 2017, Vautravers et al.
U.S. Appl. No. 15/575,169, filed Nov. 17, 2017, Rüdenauer et al.
U.S. Appl. No. 15/577,570, filed Nov. 28, 2017, Rüdenauer et al.
U.S. Appl. No. 15/577,590, filed Nov. 28, 2017, Siegel et al.
U.S. Appl. No. 15/578,959, filed Dec. 1, 2017, Bru Roig et al.
U.S. Appl. No. 15/744,324, filed Jan. 12, 2018, Parvulescu et al.
International Preliminary Report on Patentability with Written Opinion for PCT/EP2016/066923, dated Jan. 25, 2018.
International Search Report for PCT/EP2016/066923 dated Sep. 27, 2016.
International Search Report for PCT/EP2016/066939 dated Sep. 13, 2016.
Written Opinion of the International Searching Authority for PCT/EP2016/066923 dated Sep. 27, 2016.
Written Opinion of the International Searching Authority for PCT/EP2016/066939 dated Sep. 13, 2016.
Baerlocher et al., "Atlas of Zeolite Framework Types", 6th Revised Edition, Elsevier, Amsterdam, 405 pages (2007). Partial Reference.
Bauer et el., "Common Fragrance and Flavor Materials, Preparation, Properties and Uses", Fourth Completely Revised Edition, 300 pages (2001).
Innes et al., "p-Methylstyrene From Tolune and Acetaldehyde", Journal of Molecular Catalysis, vol. 32, pp. 259-271, 1985.
Maslozhirovaya Promyshiennost, vol. 9, pp. 29-32 (1974) (English translation not available).

PROCESS FOR PREPARING AN ARYLPROPENE

CROSS-REFERENCE TO RELATED APPLICATIONS

This application is a national stage application (under 35 U.S.C. § 371) of PCT/EP2016/066923, filed Jul. 15, 2016, which claims benefit of European Application No. 15176820.7, filed Jul. 15, 2015, both of which are incorporated herein by reference in their entirety.

The present invention relates to a gas phase thermolysis process for preparing an arylpropene from a diarylpropane wherein a thermolysis catalyst is employed which comprises a boron containing zeolitic material.

Anethole, due to its characteristic anis smell, is of significant commercial interest as a fragrance and as a flavouring substance. In particular, anethole is used as a fragrance in detergents and cleaning agents as well as a flavouring substance in the food industry.

Certain synthesis procedures for preparing anethole are known in the art. For example, anethole can be prepared from natural sources such as fennel oil or anise oil. Reference is made, for example, to CN 102491884 A. However, the preparation of fragrances from natural sources is often expensive, and the amounts obtainable by this processes are only limited. Further, the purity or the obtained amounts of these fragrances often vary due to changing environmental conditions. Therefore, there is a need to at least partially replace said natural sources by synthetically obtainable compounds.

With regard to such synthetically obtainable compounds, Bauer et al., Common Fragrance and Flavor Materials, 2001, 4th Edition, Wiley-VHC, describes the preparation of anethole by a process which comprises the base catalyzed re-arrangement of 1-allyl-4-methoxybenzene (estragole). Methods comprising a Friedel-Crafts acylation of methoxybenzene (anisole) with propionic acid halides or propionic acid anhydride followed by the reduction of the carbonyl group and the subsequent elimination of water are disclosed in SU 261380 and SU 355144. The acylation of anisole with propionic acid anhydride with $ZnCl_2$ and $FeCl_3$ is described in Maslozhirovaya Promyshlennost (1974), volume 9, pages 29-30. CN 103058835 A describes a process for the synthesis of anethole via a Friedel-Crafts reaction starting from anisole and propionic acid chloride, followed by the reduction of th carbonyl group to obtain the corresponding alcohol using $NaBH_4$ and the subsequent elimination of water. DE 2418974 B1 describes a process for the preparation of anethole wherein, in a first step, anisole is condensed with propionic aldehyde in the presence of acidic catalysts to obtain a mixture of bis-(methoxyphenyl) propanes, and in a second step, the condensation products are decomposed in the liquid phase in the presence of catalytic amounts of acid at a a temperature of from 100 to 300° C. to obtain trans-anethole, cis-anethole and anisole; it is a disadvantage of this process that the bis-(methoxyphenyl) propanes are not completely decomposed; additionally, only moderate yields regarding anethole are obtained; yet further, the long exposure time of the bis-(methoxyphenyl) propanes at elevated temperatures leads to an increased amount of by-products, non-desired isomers as well as oligomers and polymers.

Therefore, it was an object of the present invention to provide an improved process for preparing arylpropenes, in particular anethole, wherein the above discussed disadvantages are avoided. It was further object of the present invention that this process is simple and efficient in order to provide the possibility to produce arylpropenes, in particular anethole, in a cost-effective manner. It was a further object of the present invention that this process exhibits a high selectivity with regard to a specific isomer of the arylpropenes, in particular to trans-anethole.

Surprisingly, it was found that these objects can be solved if in a gas phase thermolysis reaction wherein a 1,1-diarylpropane is decomposed to the respective arylpropene, a solid catalyst is employed which comprises, as catalytically active material, a boron containing zeolitic material which exhibits a specific pore system.

Therefore, the present invention relates to a process for preparing a compound of formula (I)

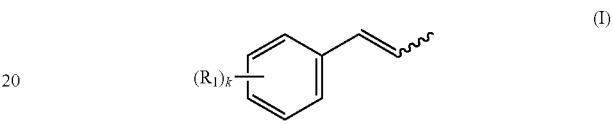

comprising contacting a compound of formula (II)

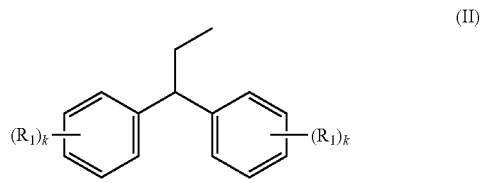

in the gas phase with a solid catalyst comprising a boron containing zeolitic material comprising a membered ring (MR) pore system greater than 10 MR, wherein k is, independently from each other, 0, 1, 2 or 3;

$R_1$ is, independently from each other, hydroxy, $C_1$-$C_6$ alkoxy, di($C_1$-$C_6$-alkyl) aminyl; wherein in the boron containing zeolitic material, the molar ratio of silicon, calculated as elemental silicon, relative to boron, calculated as elemental boron, is in the range of from 1:1 to 100:1.

Further, it was found that by carrying out the process in the gas phase in the presence of the catalyst comprising a boron containing zeolitic material, high temperatures are possible which allow to minimize the exposure time in the reaction zone in which the reaction is carried out. Therefore, it was possible to minimize the formation of by-products and side-products. In particular, it was found that the combination of the gas phase reaction with the catalyst comprising a boron containing zeolitic material leads to highly selective process with regard to the formation of the trans-isomer of the compound of formula (I-a), preferably trans-anethole. These advantages could be realized based on a high conversion of the starting material, the compound of formula (II), although, as mentioned above, the exposure time in the reaction zone was short.

The compound of formula (II) can be prepared according any conceivable and suitable process. Suitably processes are described, for example, in DE 2418974 B1.

The term "boron containing zeolitic material" as used according to the present invention relates to a zeolitic material which contains boron as part of its zeolitic microporous framework. In addition to the boron contained in the framework, the zeolitic material may further comprise extra-framework boron. The boron in the framework is bridging neighboring oxygen atoms of the framework; therefore, formally, the boron containing zeolitic material can be described as comprising $B_2O_3$ in the framework.

With regard to the pore system, no specific restrictions exist provided that the boron containing zeolitic material comprises at least one MR pore system greater 10 MR. Preferably, the boron containing zeolitic material comprises a 12 MR pore system. Generally, the boron containing zeolitic material may comprise at least one MR pore system of 10 MR or less. Preferably, if the boron containing zeolitic material comprises an MR pore system of 10 MR or less, it comprises an MR pore system of 10 MR. Preferred framework types of the boron containing zeolitic material include, but are not restricted to, MWW and BEA. The three-letter codes "MWW" and "BEA" used above refer to unique structure topologies of the different zeolite types; these three-letter codes are, for example, defined in Baerlocher et al., Atlas of Zeolite Framework Types, 6th revised edition (2007), Elsevier, Amsterdam.

According to a first preferred embodiment, the MR pore system of the boron containing zeolitic material consists of a 12 MR pore system. With regard to the respective zeolitic framework type, no specific restrictions exist. Preferably, the boron containing zeolitic material comprises, preferably has, framework type BEA.

According to a second preferred embodiment, the MR pore system of the boron containing zeolitic material consists of a 12 MR pore system and a 10 MR. With regard to the respective zeolitic framework type, no specific restrictions exits. Preferably, the boron containing zeolitic material comprises, preferably has, framework type MWW.

Therefore, the present invention preferably relates to a process for preparing a compound of formula (I)

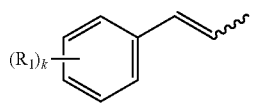

(I)

comprising contacting a compound of formula (II)

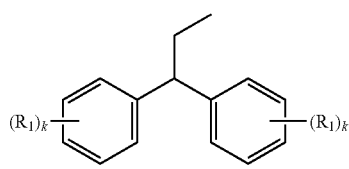

(II)

in the gas phase with a solid catalyst comprising a boron containing zeolitic material comprising a membered ring (MR) pore system greater than 10 MR and having framework type MWW or BEA, preferably MWW, wherein k is, independently from each other, 0, 1, 2 or 3;

$R_1$ is, independently from each other, hydroxy, $C_1$-$C_6$ alkoxy, di($C_1$-$C_6$-alkyl) aminyl; wherein in the boron containing zeolitic material, the molar ratio of silicon, calculated as elemental silicon, relative to boron, calculated as elemental boron, is in the range of from 1:1 to 100:1.

The term "$C_1$-$C_6$ alkoxy" as used in the context of the present invention relates to a linear or branched alkyl residue having 1, 2, 3, 4, 5, or 6 carbon atoms wherein the alkyl residue is linked to the phenyl residue via an oxygen atom. Preferred $C_1$-$C_6$ alkoxy residues include methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy. If a residue $R_1$ is $C_1$-$C_6$ alkoxy, it is preferably $C_1$-$C_5$ alkoxy, more preferably $C_1$-$C_4$ alkoxy, more preferably $C_1$-$C_3$ alkoxy, more preferably $C_1$-$C_2$ alkoxy. If $R_1$ is $C_1$-$C_6$ alkoxy, it is more preferably methoxy.

The term "di($C_1$-$C_6$-alkyl) aminyl" as used in the context of the present invention relates to a residue wherein 1 first $C_1$-$C_6$-alkyl group and a second $C_1$-$C_6$-alkyl group are linked via a nitrogen atom to the phenyl residue. The term "$C_1$-$C_6$-alkyl" as used in the context of the present invention relates to a linear or branched alkyl residue having 1, 2, 3, 4, 5, or 6 carbon atoms. Further, the first $C_1$-$C_6$-alkyl group can be identical to or different from the second $C_1$-$C_6$-alkyl group. In preferred di($C_1$-$C_6$-alkyl) aminyl residues, the $C_1$-$C_6$-alkyl includes methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl. If a residue $R_1$ is di($C_1$-$C_6$-alkyl) aminyl, the $C_1$-$C_6$-alkyl is preferably $C_1$-$C_5$ alkyl, more preferably $C_1$-$C_4$ alkyl, more preferably $C_1$-$C_3$ alkyl.

With regard to the position of the phenyl residue at which a given residue $R_1$ is located, no specific restrictions exist. Generally, it is conceivable that a given residue $R_1$ is located at every suitably ortho- and/or meta- and/or para-position. Further, it is conceivable that one of the phenyl residues of the compound of formula (II) has 0 or 1 or 2 or 3 residues $R_1$ which may be the same or different from each other, and the other phenyl residue of the compound of formula (II) has 0 or 1 or 2 or 3 residues $R_1$ which may be the same or different from each other.

More preferably, a given residue $R_1$ is hydroxy or methoxy. More preferably, each $R_1$ is methoxy.

Preferably, at least one of the phenyl residues of the compound of formula (II) has one (single) residue $R_1$ which, more preferably, is located at the para-position. More preferably, each of the two phenyl residues of the compound of formula (II) has one (single) residue $R_1$ which, more preferably, is located at the para-position wherein the residues $R_1$ may be the same or different from each other, wherein it is more preferred that the two residues $R_1$ are the same.

Therefore, the present invention preferably relates to the process as described above wherein the compound of formula (I) is a compound of formula

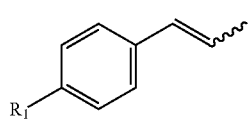

(I)

and the compound of formula (II) is a compound of formula

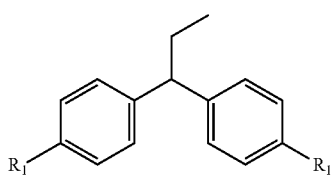

wherein the two residues $R_1$ according to formula (II) are preferably the same. Further preferably, the present invention relates to the process as described above wherein the compound of formula (I) is a compound of formula

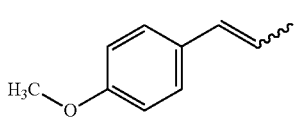

and the compound of formula (II) is a compound of formula

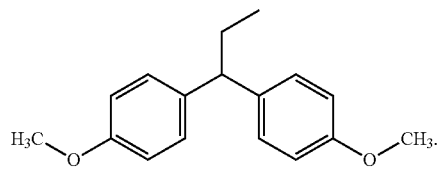

Consequently, the present invention preferably relates to a process for preparing a compound of formula (I)

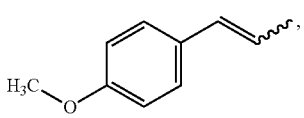

comprising contacting a compound of formula (II)

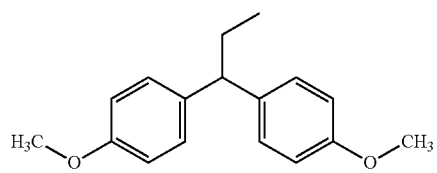

in the gas phase with a solid catalyst comprising a boron containing zeolitic material comprising a membered ring (MR) pore system greater than 10 MR and having framework type MWW or BEA, preferably MWW, wherein in the boron containing zeolitic material, the molar ratio of silicon, calculated as elemental silicon, relative to boron, calculated as elemental boron, is in the range of from 1:1 to 100:1.

In particular in case the compound of formula (II) is a compound of formula

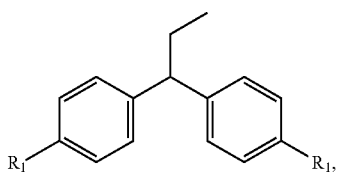

preferably

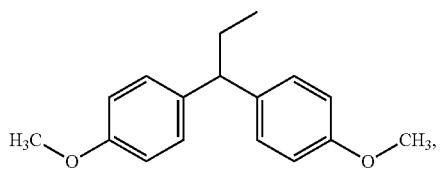

the starting material which is subjected to the contacting with the catalyst comprising a boron containing zeolitic material is optionally a mixture comprising the compound of formula (II), i.e. the para/para-substituted (pp) dimer, the ortho/para-substituted (op) dimer of formula (II-b)

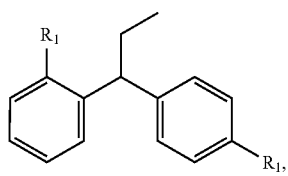

preferably

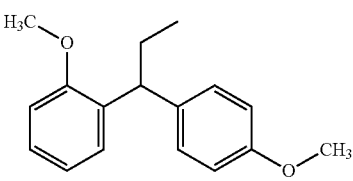

and the ortho/ortho-substituted (oo) dimer of formula (II-c)

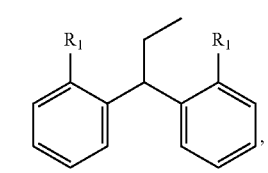

preferably

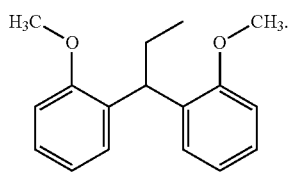

Preferably, the molar ratio of (II) relative to the sum of (II), (II-b) and (II-c) is in the range of from 65 to 75%, the molar ratio of (II-b) relative to the sum of (II), (II-b) and (II-c) is in the range of from 25 to 30%, and the molar ratio of (II-c) relative to the sum of (II), (II-b) and (II-c) is in the range of from 1 to 5%, wherein for a given mixture, these molar ratios add up to 100%. A specifically preferred mixture comprises from 69 to 71% (II) such as 70% (II), from 27 to 29% (II-b), such as 28% (II-b), and from 1 to 3% (II-c), such as 2% (II-c), in each based on the sum of (II), (II-b) and (II-c).

Therefore, the present invention also relates to a process as described above wherein the compound of formula (I) is a compound of formula (I)

and the compound of formula (II) is a compound of formula (II)

wherein the two residues $R_1$ according to formula (II) are preferably the same, and wherein, prior to the contacting with the catalyst comprising a boron containing zeolitic material, the gas phase comprises, in addition to the compound of formula (II), the compound of formula (II-b)

(II-b)

and the compound of formula (II-c)

(II-c)

wherein the molar ratio of (II) relative to the sum of (II), (II-b) and (II-c) is preferably in the range of from 65 to 75%, the molar ratio of (II-b) relative to the sum of (II), (II-b) and (II-c) is preferably in the range of from 25 to 30%, and the molar ratio of (II-c) relative to the sum of (II), (II-b) and (II-c) is preferably in the range of from 1 to 5% wherein more preferably, these molar ratios add up to 100%.

Further preferably, the present invention relates to the process as described above wherein the compound of formula (I) is a compound of formula (I)

and the compound of formula (II) is a compound of formula (II)

wherein, prior to the contacting with the catalyst comprising a boron containing zeolitic material, the gas phase comprises, in addition to the compound of formula (II), the compound of formula (II-b)

(II-b)

and the compound of formula (II-c)

(II-c)

wherein the molar ratio of (II) relative to the sum of (II), (II-b) and (II-c) is preferably in the range of from 65 to 75%, the molar ratio of (II-b) relative to the sum of (II), (II-b) and (II-c) is preferably in the range of from 25 to 30%, and the molar ratio of (II-c) relative to the sum of (II), (II-b) and (II-c) is preferably in the range of from 1 to 5% wherein more preferably, these molar ratios add up to 100%.

With regard to the specific composition of the boron containing zeolitic material, no specific restrictions exist. Preferably, in the boron containing zeolitic material, the molar ratio of silicon, calculated as elemental silicon, relative to boron, calculated as elemental boron, is in the range of from 5:1 to 50:1, preferably in the range of from 10:1 to 20:1. More preferably, this molar ratio is in the range of from 11:1 to 18:1, more preferably in the range of from 12:1 to 16:1. These molar ratios relate to the molar ratios of the boron and the silicon which are contained in the framework of the boron containing zeolitic material.

Generally, the framework of the boron containing zeolitic material comprises boron, silicon, oxygen and hydrogen. In addition to boron, silicon, oxygen and hydrogen, the framework of the boron containing zeolitic material may comprise at least one further trivalent element and/or at least one further tetravalent element and/or at least further pentavalent element, such as one or more of Ti, Al, Zr, V, Nb, Ta, Cr, Mo, W, Mn, Fe, Co, Ni, Zn, Ga, Ge, In, Pb. In addition to the elements constituting the framework, the boron containing zeolitic material may comprise at least one extra-framework elements, such as one or more of B, Ti, Al, Zr, V, Nb, Ta, Cr, Mo, W, Mn, Fe, Co, Ni, Zn, Ga, Ge, In, Sn, Pb.

Preferably, at least 90 weight-%, more preferably at least 95 weight-%, more preferably at least 99 weight-%, more preferably at least 99.5 weight-%, more preferably at least 99.9 weight-% of the framework of the boron containing zeolitic material consist of boron, silicon, oxygen, and hydrogen. More preferably, at least 90 weight-%, more preferably at least 95 weight-%, more preferably at least 99 weight-%, more preferably at least 99.5 weight-%, more preferably at least 99.9 weight-% of the boron containing zeolitic material consist of boron, silicon, oxygen, and hydrogen. More preferably, the boron containing zeolitic material essentially consists of boron, silicon, oxygen, and hydrogen, wherein the term "essentially consists of" as used in this specific context refers to a boron containing zeolitic material which, in addition to boron, silicon, oxygen, and hydrogen, comprises, if at all, other elements only as impurities which are unavoidable in view of the process for the preparation of the boron containing zeolitic material.

Therefore, the present invention preferably relates to a process for preparing a compound of formula (I)

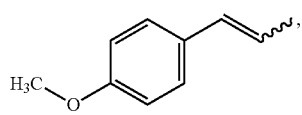

(I)

comprising contacting a compound of formula (II)

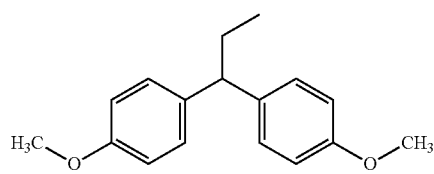

(II)

in the gas phase with a solid catalyst comprising a boron containing zeolitic material comprising a membered ring (MR) pore system greater than 10 MR and having framework type MWW or BEA, preferably MWW, wherein in the boron containing zeolitic material, the molar ratio of silicon, calculated as elemental silicon, relative to boron, calculated as elemental boron, is in the range of from 1:1 to 100:1 and wherein at least 95 weight-%, preferably at least 99 weight-%, more preferably at least 99.5 weight-%, more preferably at least 99.9 weight-% of the framework of the boron containing zeolitic material, preferably 95 weight-%, preferably at least 99 weight-%, more preferably at least 99.5 weight-%, more preferably at least 99.9 weight-% of the boron containing zeolitic material, consist of boron, silicon, oxygen, and hydrogen.

Generally, it is possible that the catalyst comprising boron containing zeolitic material consists of the boron containing zeolitic material. According to this embodiment, it is possible that the boron containing zeolitic material is used as a powder, as a spray powder which is prepared, for example, by spray drying or by spray granulation, as a compacted powder in the form of shaped bodies such as tablets or the like.

Preferably, the catalyst comprising boron containing zeolitic material comprises, in addition to the boron containing zeolitic material, a binder material wherein the catalyst is in the form of a molding. As described hereinunder in detail, the process of the present invention is preferably carried out in continuous mode. For said continuous process, it is preferred that the solid porous catalyst comprising silica is employed in the form of moldings. As to the geometry of the moldings, no specific restrictions exist. Geometries such as strands, for example having rectangular, triangular hexagonal, quadratic, oval, or circular cross-section, stars, tablets, spheres, hollow cylinders, and the like are possible. A preferred geometry of the moldings is a strand having circular cross-section. Such a geometry is preferred if the moldings are employed, for example, as fixed-bed catalyst or fluidized-bed catalyst, more preferably in continuous-type reactions. The diameter of these strands having circular cross-section which can be prepared, e.g., via extrusion processes, is preferably in a range of from 1 to 5 mm, more preferably from 1 to 4 mm, more preferably from 1 to 3 mm, such as, for example, in the range of from 1 to 2 mm or in the range of from 1.5 to 2.5 mm or in the range of from 2 to 3 mm.

In general, suitable binders are all compounds which impart adhesion and/or cohesion between the boron containing zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaolin, hectorite, bentonites, halloysites, dickites, nacrites or anaxites. In the preparation of the catalysts of the present invention, these binders can be used as such or in the form of suitable precursor compounds which, either during spray-drying and/or calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention, binders which either completely or partly comprise $SiO_2$, or which are a precursor of $SiO_2$ from which $SiO_2$ is formed, are preferred. In this context, both colloidal silica and so-called "wet process" silica and so-called "dry process" silica can be used. This silica may be amorphous silica, the size of the silica particles being, for example, in the range of from 5 to 100 nm and the surface area of the silica particles being in the range of from 50 to 500 m²/g. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica can be preferred.

Preferably at least 75 weight-%, more preferably at least 80 weight-%, more preferably at least 85 weight-%, more preferably at least 90 weight-%, more preferably at least 95 weight-%, more preferably at least 99 weight-%, more preferably at least 99.5 weight-%, more preferably at least 99.9 weight-% of the binder material consist of silica.

As to the ratio of the amount of present zeolitic material relative to the amount of binder used for preparing a molding, it generally can be freely chosen. Preferably, the weight ratio of the boron containing zeolitic material relative to binder is in the range of from 5:1 to 50:1, more preferably in the range of from 10:1 to 25:1, more preferably in the range of from 15:1 to 20:1.

Generally, it is conceivable that the catalyst, in addition to the boron containing zeolitic material and the binder, contains one or more further compounds. Preferably, at least 99 weight-%, preferably at least 99.5 weight-%, more preferably at least 99.9 weight-% of the catalyst consist of the boron containing zeolitic material and the binder material. More preferably, the catalyst essentially consists of the boron containing zeolitic material and the binder, wherein the term "essentially consists of" as used in this specific context refers to a catalyst which, in addition to the boron containing zeolitic material and the binder, comprises, if at all, other elements or compounds only as impurities which are unavoidable in view of the process for the preparation of the catalyst.

Therefore, the present invention preferably relates to a process for preparing a compound of formula (I)

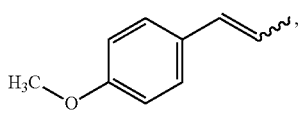
(I)

comprising contacting a compound of formula (II)

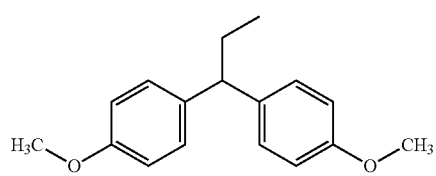
(II)

in the gas phase with a solid catalyst comprising a boron containing zeolitic material comprising a membered ring (MR) pore system greater than 10 MR and having framework type MWW or BEA, preferably MWW, wherein in the boron containing zeolitic material, the molar ratio of silicon, calculated as elemental silicon, relative to boron, calculated as elemental boron, is in the range of from 1:1 to 100:1 and wherein at least 95 weight-%, preferably at least 99 weight-%, more preferably at least 99.5 weight-%, more preferably at least 99.9 weight-% of the framework of the boron containing zeolitic material, preferably 95 weight-%, preferably at least 99 weight-%, more preferably at least 99.5 weight-%, more preferably at least 99.9 weight-% of the boron containing zeolitic material, consist of boron, silicon, oxygen, and hydrogen and wherein at least 99 weight-%, preferably at least 99.5 weight-%, more preferably at least 99.9 weight-% of the catalyst consist of the boron containing zeolitic material and a binder material of which at least 99 weight-%, preferably at least 95 weight-%, more preferably at least 99.9 weight-% consist of silica.

Preferably, the contacting of the compound of formula (II) with the solid catalyst comprising a boron containing zeolitic material is carried out under thermolytic conditions. The temperature of the gas phase at which said contacting is carried out is preferably at least 250° C., more preferably in the range of from 250 to 650° C., more preferably in the range of from 260 to 600° C., more preferably in the range of from 270 to 550° C., more preferably in the range of from 280 to 500° C., more preferably in the range of from 290 to 450° C., more preferably in the range of from 300 to 400° C. Preferred ranges are, for example, of from 300 to 350° C. or from 325 to 375° C. or from 350 to 400° C. The absolute pressure of the gas phase at which said contacting is carried out is preferably in the range of from 0.1 to 2.0 bar, preferably in the range of from 0.5 to 1.5 bar, more preferably in the range of from 0.8 to 1.1 bar. Therefore, it is preferred that the contacting of the compound of formula (II) with the solid catalyst comprising a boron containing zeolitic material is carried out at a temperature of the gas phase in the range of from 300 to 400° C. and an absolute pressure of the gas phase in the range of from 0.8 to 1.1 bar.

Generally, it is conceivable that the gas phase which is brought into contact with the solid catalyst consists of the gaseous compound of formula (II) and optionally a carrier gas which is described hereinunder. Preferably, the gas phase which is brought into contact with the solid catalyst comprises the gaseous compound of formula (II), optionally a carrier gas, and a diluent.

Preferably, the comprises, more preferably consists of, one or more of optionally substituted aliphatic hydrocarbon, optionally aromatic hydrocarbon, ether, alkylnitrile, alkanol, water. More preferably, the diluent comprises, more preferably consists of, one or more of pentane, hexane, heptane, petroleum ether, cyclohexane, dichloromethane, trichloromethane, tetrachloromethane, benzene, toluene, xylene, chlorobenzene, dichlorobenzene, diethylether, methyl-tert-butylether, dibutylether, tetrahydrofuran, dioxane, acetonitrile, propionitrile, methanol, ethanol, water. More preferably, the diluent comprises, preferably consists of, one or more of diethylether, methyl-tert-butylether, tetrahydrofuran, acetonitrile, water. More preferably, the diluent comprises water. More preferably, at least 0.3 weight-%, preferably at least 1 weight-%, more preferably at least 10 weight-%, more preferably at least 50 weight-%, more preferably at least 99 weight-%, more preferably at least 99.9 weight-% of the diluent consist of water. More preferably, the diluent is water.

With regard to the amount of diluent used, no specific restrictions exist, and the weight ratio of the diluent relative to the compound of formula (II) can be varied in wide ranges. Preferably, prior to contacting the compound of formula (II) with the solid catalyst comprising a boron containing zeolitic material, the weight ratio of the diluent relative to the compound of formula (II) is in the range of from 20:1 to 1:100, preferably in the range of from 10:1 to 1:10, more preferably in the range of from 5:1 to 1:1.

While it is generally conceivable that contacting the compound of formula (II) with the solid catalyst comprising a boron containing zeolitic material is carried out in batch mode or in semi-continous mode, it is preferred that the contacting is carried out in continuous mode. According to this continuous mode, it is possible that the compound of formula (II), in gaseous form, and preferably the diluent, in gaseous form, are passed into a suitable reaction zone, such as a tubular reactor or the like which contains the solid catalyst comprising a boron containing zeolitic material. Prior to passing the compound of formula (II), in gaseous form, and the diluent, in gaseous form, into the reaction zone, the compound of formula (II) and the diluent can be admixed with each other.

The reaction zone can be designed in all forms suitable for gas phase reactions. Usually, the reaction zone is a cylindrical or tubular reactor which is at least partially filled with the solid catalyst. The solid catalyst can be arranged in the reaction as a fixed bed, as a fluidized bed, or as a packing. The reaction zone can be arranged horizontally or vertically wherein, in case the reaction is arranged vertically, the gas phase can be passed throught the reaction zone in upstream mode or in downstream mode. Usually, for tubular reaction zones, the length of the reaction zone, i.e. the zone which is filled with the catalyst, relative to the internal diamater of the reaction zone, is at least 3:1, preferably in the range of from 3:1 to 100:1, more preferably in the range of from 5:1 to 10:1. The reaction zone is usually equipped with heating means such as electrical heating or induction heating. Preferably, an evaporation zone is arranged upstream of the reaction zone in which the compound of formula (II) and optionally the diluent are evaporated. If the reaction zone is comprised in a tubular reactor, it is possible, for example, that a first zone of the tubular reactor is designed as the evaporation zone and a downstream zone of the tubular reactor is the reaction zone comprising the solid catalyst.

For passing the compound of formula (II), in gaseous form, and the diluent, in gaseous form, into and through the reaction zone, a carrier gas can be employed. Therefore, the gas phase which is brought into contact with the catalyst comprising a boron containing zeolitic material preferably comprises a carrier gas.

No specific restrictions exist with regard to the chemical nature of the carrier gas. Preferably, the carrier gas is a gas or a mixture of two or more gases which is inert with respect to the thermolysis reaction. The term "inert" as used in this context of the present invention relates to a gas or a mixture of two or more gases which does not have a negative influence on the thermolysis reaction. Preferably, the carrier gas comprises one or more of helium, argon, nitrogen, more preferably nitrogen. More preferably, the carrier gas is nitrogen, more preferably technical nitrogen having a nitrogen content of at least 99.5 volume-% and an oxygen content of at most 0.5 volume-%.

With regard to the amount of carrier gas used, no specific restrictions exist, and the volume ratio of the carrier gas relative to the compound of formula (II) can be varied in wide ranges. Preferably, prior to contacting the compound of formula (II) with the solid catalyst comprising a boron containing zeolitic material, the volume ratio of the carrier gas relative to the compound of formula (II) in its gaseous form is in the range of from 1:1 to 20:1, preferably in the range of from 2:1 to 15:1, more preferably in the range of from 5:1 to 10:1.

With regard to the volume flow through the reaction zone comprising the solid catalyst comprising a boron containing zeolitic material, it is preferred that the achieved catalyst load is at least 0.01 kg/kg/h. The catalyst load is defined as mass of the compound of formula (II) in kg per 1 kg of the catalyst material per 1 h. Preferably, the catalyst load is in the range of from 0.01 to 5 kg (compound of formula (II))/kg (catalyst)/h, more preferably in the range of from 0.02 to 2 kg (compound of formula (II))/kg (catalyst)/h, more preferably in the range of from 0.05 to 1 kg (compound of formula (II))/kg (catalyst)/h, more preferably in the range of from 0.1 to 0.5 kg (compound of formula (II))/kg (catalyst)/h.

From the thermolysis reaction of the present invention, a reaction mixture is obtained, preferably at the exit of the reaction zone comprising the catalyst comprising the boron containing zeolitic material. Surprisingly, it was found that the use of the catalyst of the present invention leads to a very advantageous process in terms of the selectivity of the reaction with regard to the compound of formula (I). Even more surprisingly, it was found that the use of catalyst of the present invention leads to a very advantageous process in terms of the selectivity of the reaction with regard to the compound of formula (I-a)

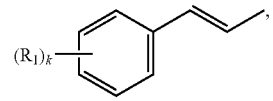

(I-a)

the trans-isomer of the compound of formula (I). Thus, it was found that the use the catalyst of the present invention leads to a very selective process with regard to the compound of formula (I-a), and thus to a reaction mixture exhibiting a very high molar ratio of the compound of formula (I-a) relative to the compound of formula (I-b)

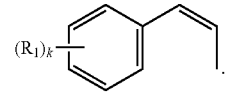

(I-b)

In particular in case the compound of formula (I) is a compound of formula

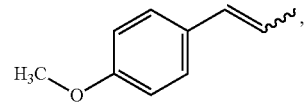

(I)

the trans-isomer is of particular commercial interest.

Therefore, the present invention also relates to the use of a boron containing zeolitic material comprising a membered ring (MR) pore system greater than 10 MR, wherein in the boron containing zeolitic material, the molar ratio of silicon, calculated as elemental silicon, relative to boron, calculated as elemental boron, is in the range of from 1:1 to 100:1, as a catalytic material for increasing the selectivity of solid catalyst gas-phase thermolysis of a compound of formula (II) with respect to the compound of formula (I-a).

Further, the present invention also relates to said reaction mixture which is directly obtained from contacting a compound of formula (II) in the gas phase with a solid catalyst comprising a boron containing zeolitic material comprising a membered ring (MR) pore system greater than 10 MR, wherein in the boron containing zeolitic material, the molar ratio of silicon, calculated as elemental silicon, relative to boron, calculated as elemental boron, is in the range of from 1:1 to 100:1, said reaction mixture comprising a compound of formula (I) comprising a compound of formula formula (I-a) and optionally a compound of formula (I-b). The term "directly obtained" as used in this context of the present invention relates to a reaction mixture which is obtained at the exit of the reaction zone in which the contacting is carried out and which is not subjected to any further treatment such as separating the compound of formula (I-a) from the compound of formula (I-b). In said reaction mixture of the present invention, the molar amount of the compound of formula (I-a) relative to the molar amount of the converted compound of formula (II), optionally—in case a mixture of the compounds of formulas (II), (II-b) and (II-c) is used as starting material—relative to the sum of the molar amounts of the converted compounds of formulas (II), (II-b) and (II-c), is at least 0.3, more preferably at least 0.4, more preferably at least 0.5, more preferably at least 0.55, more preferably at least 0.58. Since according to the present invention, the conversion of the compound of formula (II) is high, the yield with respect to the compound of formula (I) is high, and also the selectivity towards the compound of formula (I-a) is high, this reaction mixture allows for a simple and efficient work-up, for example for separating the compound of formula (I) and/or (I-a) from the reaction mixture.

After having left the reaction zone, the reaction mixture is preferably cooled, for example in a cooler arranged directly downstream the reaction zone. The cooling is preferably carried out so that the cooled reaction mixture has a temperature in the range of from 0 to 40° C., preferably in the range of from 0 to 35° C., more preferably in the range of from 0 to 30° C., more preferably in the range of from 0 to 25° C., more preferably in the range of from 0 to 20° C., more preferably in the range of from 0 to 15° C., more preferably in the range of from 0 to 10° C. Suitable coolers include, for example, intensive coolers and cold traps.

The valuable products contained in the thus cooled mixture can be separated from the mixture according to generally known methods, including extraction, distillation, crystallization or chromatographic isolation. Therefore, the present invention also relates to the process as described above, wherein the compound of formula (I) comprises a compound of formula (I-a)

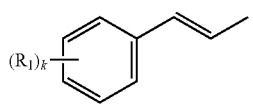

and a compound of formula (I-b)

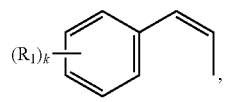

said process further comprising separating the compound of formula (I-a) from the compound of formula (I-b).

Depending on the chemical nature of the starting material, the mixture obtained from the thermolysis reaction contains a mixture of the cis-isomer and the trans-isomer or also a mixture of regioisomers comprising ortho-, meta- and/or para-substituted compounds. The separation of the individual isomers is preferably carried out by fractional distillation or chromatographic isolation. Preferably, the mixture is subjected to distillation wherein distillation columns—equipped, for example, with bubble-cup trays, sieve plates, sieve trays, packings—or rotating-strip columns or evaporators such as thin film evaporator, falling film evaporator, forced circulation evaporator, sambay evaporator and the like. More preferably, distillation columns are used, in particular rotating-strip columns.

The present invention is further illustrated by the following embodiments and combinations of embodiments as indicated by the respective dependencies and back-references.

1. A process for preparing a compound of formula (I)

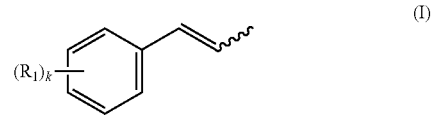

comprising contacting a compound of formula (II)

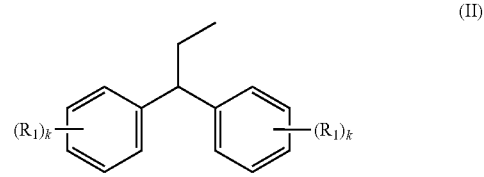

in the gas phase with a solid catalyst comprising a boron containing zeolitic material comprising a membered ring (MR) pore system greater than 10 MR, wherein k is, independently from each other, 0, 1, 2 or 3;

$R_1$ is, independently from each other, hydroxy, $C_1$-$C_6$ alkoxy, di($C_1$-$C_6$-alkyl) aminyl; wherein in the boron containing zeolitic material, the molar ratio of silicon, calculated as elemental silicon, relative to boron, calculated as elemental boron, is in the range of from 1:1 to 100:1.

2. The process of embodiment 1, wherein the boron containing zeolitic material comprises a 12 MR pore system, the boron containing zeolitic material preferably having a framework type MWW or a framework type BEA.

3. The process of embodiment 1 or 2, wherein the MR pore system of the boron containing zeolitic material consists of the 12 MR pore system.

4. The process of embodiment 2 or 3, wherein the boron containing zeolitic material has framework type BEA.

5. The process of embodiment 1 or 2, wherein the boron containing zeolitic material comprises a 12 MR pore system and a 10 MR pore system.

6. The process of embodiment 5, wherein the MR pore system of the boron containing zeolitic material consists of the 12 MR pore system and the 10 MR pore system.

7. The process of embodiment 5 or 6, wherein the boron containing zeolitic material has framework type MWW.

8. A process for preparing a compound of formula (I)

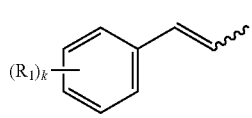
(I)

comprising contacting a compound of formula (II)

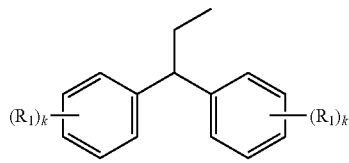
(II)

in the gas phase with a solid catalyst comprising a boron containing zeolitic material comprising a membered ring (MR) pore system greater than 10 MR and having framework type MWW, wherein k is, independently from each other, 0, 1, 2 or 3;

$R_1$ is, independently from each other, hydroxy, $C_1$-$C_6$ alkoxy, di($C_1$-$C_6$-alkyl) aminyl; wherein in the boron containing zeolitic material, the molar ratio of silicon, calculated as elemental silicon, relative to boron, calculated as elemental boron, is in the range of from 1:1 to 100:1.

9. The process of any one of embodiments 1 to 8, wherein $C_1$-$C_6$ alkoxy includes methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy.

10. The process of any one of embodiments 1 to 9, wherein in di($C_1$-$C_6$-alkyl) aminyl, the $C_1$-$C_6$-alkyl includes methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl.

11. The process of any one of embodiments 1 to 10, wherein $R_1$ is, independently from each other, hydroxy, $C_1$-$C_4$-alkoxy, di($C_1$-$C_3$-alkyl)aminyl, preferably hydroxy, $C_1$-$C_3$-alkoxy, di($C_1$-$C_3$-alkyl)-aminyl, more preferably hydroxy, $C_1$-$C_3$-alkoxy, more preferably hydroxy, $C_1$-$C_2$-alkoxy.

12. The process of any one of embodiments 1 to 11, wherein the compound of formula (I) is a compound of formula

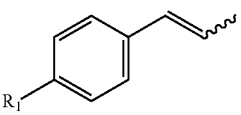
(I)

and the compound of formula (II) is a compound of formula

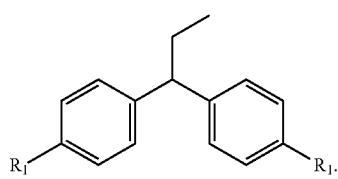
(II)

13. The process of any one of embodiments 1 to 12, preferably of embodiment 12, wherein $R_1$ is hydroxy or methoxy.

14. The process of any one of embodiments 1 to 13, wherein the compound of formula (I) is a compound of formula

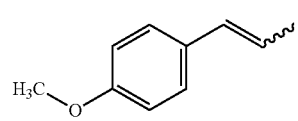
(I)

and the compound of formula (II) is a compound of formula

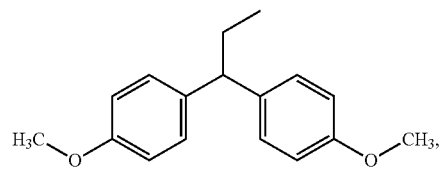
(II)

wherein, prior to the contacting with the catalyst comprising a boron containing zeolitic material, the gas phase optionally comprises, in addition to the compound of formula (II), the compound of formula (II-b)

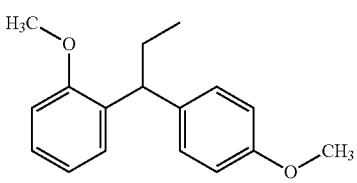
(II-b)

and the compound of formula (II-c)

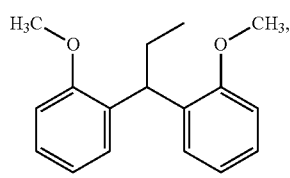
(II-c)

wherein the molar ratio of the compound of formula (II) relative to the sum of the compound of formula (II), the compound of formula (II-b) and the compound of formula (II-c) is preferably in the range of from 65 to 75%, the molar ratio of the compound of formula (II-b) relative to the sum of the compound of formula (II), the compound of formula (II-b) and the compound of formula (II-c) is preferably in the range of from 25 to 30%, and the molar ratio of the compound of formula (II-c) relative to the sum of the compound of formula (II), the compound of formula (II-b) and the compound of formula (II-c) is preferably in the range of from 1 to 5% wherein more preferably, these molar ratios add up to 100%.

15. A process for preparing a compound of formula (I)

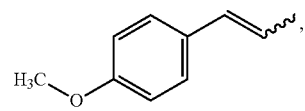

comprising contacting a compound of formula (II)

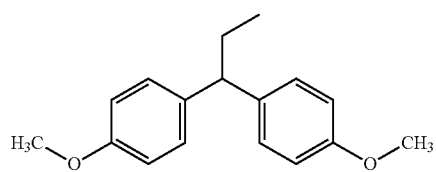

in the gas phase with a solid catalyst comprising a boron containing zeolitic material comprising a membered ring (MR) pore system greater than 10 MR and having framework type MWW,
wherein in the boron containing zeolitic material, the molar ratio of silicon, calculated as elemental silicon, relative to boron, calculated as elemental boron, is in the range of from 1:1 to 100:1.

16. The process of any one of embodiments 1 to 15, wherein in the boron containing zeolitic material, the molar ratio of silicon, calculated as elemental silicon, relative to boron, calculated as elemental boron, is in the range of from 5:1 to 50:1, preferably in the range of from 10:1 to 20:1, more preferably in the range of from 11:1 to 18:1, more preferably in the range of from 12:1 to 16:1.

17. The process of any one of embodiments 1 to 16, wherein at least 99 weight-%, preferably at least 99.5 weight-%, more preferably at least 99.9 weight-% of the boron containing zeolitic material consists of boron, silicon, oxygen, and hydrogen.

18. The process of any one of embodiments 1 to 18, wherein the solid catalyst further comprises a binder material.

19. The process of embodiment 18, wherein at least 75 weight-%, preferably at least 90 weight-%, more preferably at least 95 weight-%, more preferably at least 99 weight-%, more preferably at least 99.9 weight-% of the binder material consist of silica.

20. The process of embodiment 18 or 19, wherein in the catalyst, the weight ratio of the boron containing zeolitic material relative to the binder material is in the range of from 5:1 to 50:1, preferably in the range of from 10:1 to 25:1, more preferably in the range of from 15:1 to 20:1.

21. The process of any one of embodiments 18 to 20, wherein at least 99 weight-%, preferably at least 99.5 weight-%, more preferably at least 99.9 weight-% of the catalyst consist of the boron containing zeolitic material and the binder material.

22. The process of any one of embodiments 1 to 21, wherein contacting the compound of formula (II) with the solid catalyst comprising a boron containing zeolitic material is carried out under thermolytic conditions.

23. The process of any one of embodiments 1 to 22, wherein contacting the compound of formula (II) with the solid catalyst comprising a boron containing zeolitic material is carried out at a temperature of the gas phase in the range of from 250 to 650° C., preferably in the range of from 260 to 600° C., more preferably in the range of from 270 to 550° C., more preferably in the range of from 280 to 500° C., more preferably in the range of from 290 to 450° C., more preferably in the range of from 300 to 400° C.

24. The process of any one of embodiments 1 to 23, wherein contacting the compound of formula (II) with the solid catalyst comprising a boron containing zeolitic material is carried out at an absolute pressure of the gas phase in the range of from 0.1 to 2.0 bar, preferably in the range of from 0.5 to 1.5 bar, more preferably in the range of from 0.8 to 1.1 bar.

25. The process of any one of embodiments 1 to 24, wherein contacting the compound of formula (II) with the solid catalyst comprising a boron containing zeolitic material is carried out in the presence of a diluent.

26. The process of embodiment 25, wherein the diluent comprises, preferably consists of, one or more of optionally substituted aliphatic hydrocarbon, optionally aromatic hydrocarbon, ether, alkylnitrile, alkanol, water.

27. The process of embodiment 25 or 26, wherein the diluent comprises, preferably consists of, one or more of pentane, hexane, heptane, petroleum ether, cyclohexane, dichloromethane, trichloromethane, tetrachloromethane, benzene, toluene, xylene, chlorobenzene, dichlorobenzene, diethylether, methyl-tert-butylether, dibutylether, tetrahydrofuran, dioxane, acetonitrile, propionitrile, methanol, ethanol, water.

28. The process of any one of embodiments 25 to 27, wherein the diluent comprises, preferably consists of, one or more of diethylether, methyl-tert-butylether, tetrahydrofuran, acetonitrile, water.

29. The process of any one of embodiments 25 to 28, wherein at least 0.3 weight-%, preferably at least 1 weight-%, more preferably at least 10 weight-%, more preferably at least 50 weight-%, more preferably at least 99 weight-%, more preferably at least 99.9 weight-% of the diluent consist of water, wherein more preferably, the diluent is water.

30. The process of any one of embodiments 1 to 29, wherein prior to contacting the compound of formula (II) with the solid catalyst comprising a boron containing zeolitic material, the weight ratio of the diluent relative to the compound of formula (II) is in the range of from 20:1 to 1:100, preferably in the range of from 10:1 to 1:10, more preferably in the range of from 5:1 to 1:1.

31. The process of any one of embodiments 1 to 30, being carried out in continuous mode.

32. The process of any one of embodiment 1 to 31, preferably 31, wherein contacting the compound of formula (II) in the gas phase with the solid catalyst comprising a boron containing zeolitic material comprising a membered ring (MR) pore system greater than 10 MR is carried out in a reaction zone comprising the solid catalyst, the process comprising passing, preferably continuously passing, the gas phase comprising the compound of formula (II) and optionally the diluent into and through the reaction zone comprising the solid catalyst.

33. The process of any one of embodiments 1 to 32, wherein the gas phase further comprises a carrier gas.
34. The process of embodiment 33, wherein the carrier gas comprises one or more of helium, argon, nitrogen, preferably nitrogen, wherein more preferably, the carrier gas is nitrogen, more preferably technical nitrogen.
35. The process of embodiment 33 or 34, wherein prior to contacting the compound of formula (II) with the solid catalyst comprising a boron containing zeolitic material, the volume ratio of the carrier gas relative to the compound of formula (II) in its gaseous form is in the range of from 1:1 to 20:1, preferably in the range of from 2:1 to 15:1, more preferably in the range of from 5:1 to 10:1.
36. The process of any one of embodiments 1 to 35, wherein contacting the compound of formula (II) with the solid catalyst comprising a boron containing zeolitic material is carried out at a catalyst load in the range of from 0.01 to 5 kg (compound of formula (II))/kg (catalyst)/h, preferably in the range of from 0.02 to 2 kg (compound of formula (II))/kg (catalyst)/h, more preferably in the range of from 0.05 to 1 kg (compound of formula (II))/kg (catalyst)/h, more preferably in the range of from 0.1 to 0.5 kg (compound of formula (II))/kg (catalyst)/h.
37. The process of any one of embodiments 1 to 36, further comprising cooling the reaction mixture to a temperature in the range of from 0 to 40° C., preferably in the range of from 0 to 20° C., more preferably in the range of from 0 to 10° C.
38. The process of any one of embodiments 1 to 37, wherein the compound of formula (I) comprises a compound of formula (I-a)

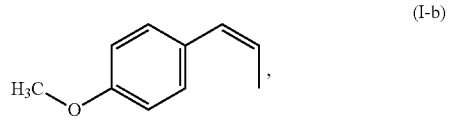
(I-a)

and a compound of formula (I-b)

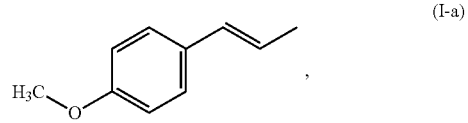
(I-b)

said process further comprising separating the compound of formula (I-a) from the compound of formula (I-b).

39. The process of embodiment 38, preferably insofar as embodiment 38 is dependent on embodiment 14, wherein the compound of formula (I) is a compound of formula

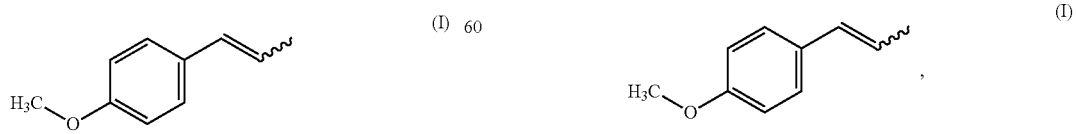
(I)

and the compound of formula (II) is a compound of formula

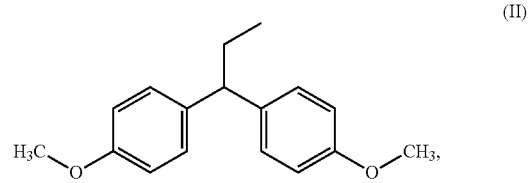 [SMILES: CCC(c1ccc(OC)cc1)c1ccc(OC)cc1]
(II)

said compound of formula (I) comprising a compound of formula (I-a)

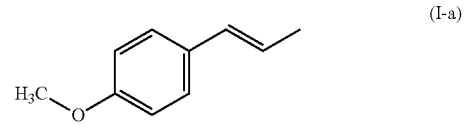
(I-a)

and a compound of formula (I-b)

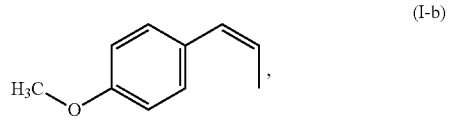
(I-b)

said process comprising separating the compound of formula (I-a) from the compound of formula (I-b).

40. A process for preparing a compound of formula (I-a)

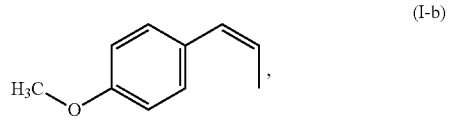
(I-a)

comprising contacting a compound of formula (II)

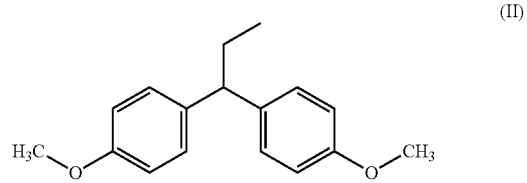
(II)

in the gas phase with a solid catalyst comprising a boron containing zeolitic material having framework type MWW, obtaining a compound of formula (I)

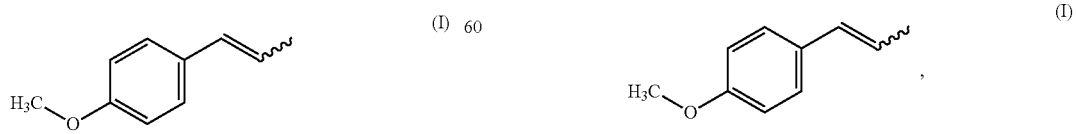
(I)

said compound of formula (I) comprising the compound of formula (I-a) and a compound of formula (I-b)

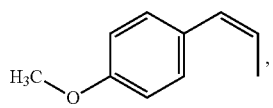

said process comprising separating the compound of formula (I-a) from the compound of formula (I-b).

41. The process of any one of embodiments 38 to 40, wherein separating the compound of formula (I-a) from the compound of formula (I-b) comprises subjecting the compound of formula (I) to distillation and/or chromatography, preferably distillation.

42. A reaction mixture, obtainable or obtained from contacting a compound of formula (II)

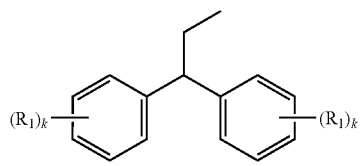

in the gas phase with a solid catalyst comprising a boron containing zeolitic material comprising a membered ring (MR) pore system greater than 10 MR, wherein k is, independently from each other, 0, 1, 2 or 3;

$R_1$ is, independently from each other, hydroxy, $C_1$-$C_6$ alkoxy, di($C_1$-$C_6$-alkyl) aminyl; wherein in the boron containing zeolitic material, the molar ratio of silicon, calculated as elemental silicon, relative to boron, calculated as elemental boron, is in the range of from 1:1 to 100:1;

said reaction mixture preferably being obtainable or obtained by a process according to any one of embodiments 1 to 36, said reaction mixture comprising a compound of formula (I)

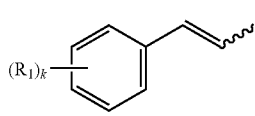

comprising a compound of formula formula (I-a)

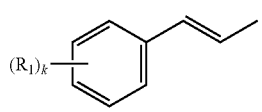

and a compound of formula (I-b)

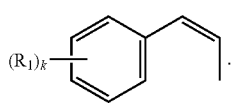

43. The reaction mixture of embodiment 42, wherein said process does not comprise separating the compound of formula (I-a) from the compound of formula (I-b).

44. The reaction mixture of embodiment 42 or 43, wherein the compound of formula (I) is

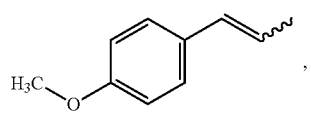

the compound of formula (II) is

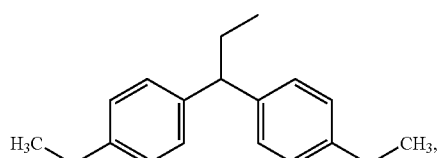

the compound of formula (I-a) is

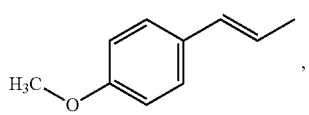

and the compound of formula (I-b) is

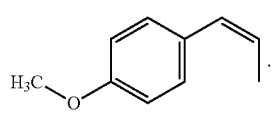

45. The reaction mixture of any one of embodiments 42 to 44, wherein the molar amount of the compound of formula (I-a) relative to the molar amount of the converted compound of formula (II), optionally relative to the sum of the molar amounts of the converted compounds of formulas (II), (II-b) and (II-c), is at least 0.3, more preferably at least 0.4, more preferably at least 0.5, more preferably at least 0.55, more preferably at least 0.58.

46. Use of a boron containing zeolitic material comprising a membered ring (MR) pore system greater than 10 MR, wherein in the boron containing zeolitic material, the molar ratio of silicon, calculated as elemental silicon, relative to boron, calculated as elemental boron, is in the range of from 1:1 to 100:1, as a catalytic material for increasing the selectivity of solid catalyst gas-phase thermolysis of a compound of formula (II)

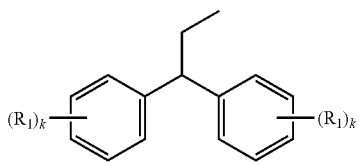

with respect to the compound of formula (I-a)

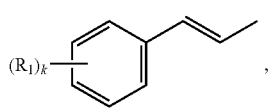

wherein k is, independently from each other, 0, 1, 2 or 3;

$R_1$ is, independently from each other, hydroxy, $C_1$-$C_6$ alkoxy, di($C_1$-$C_6$-alkyl) aminyl.

47. The use of embodiment 46, wherein the boron containing zeolitic material comprising a membered ring (MR) pore system greater than 10 MR is as defined in any one of embodiments 2 to 14, preferably as defined in embodiment 6 or 7, more preferably as defined in embodiment 7, more preferably as defined in embodiments 9 and 10 insofar embodiments 9 and 10 is dependent of embodiment 7.

48. The use of embodiment 46 or 47, wherein the compound of formula (II) is

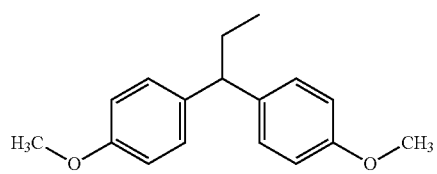
(II)

and the compound of formula (I-a) is

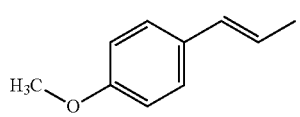
(I-a)

49. A method of increasing the selectivity of solid catalyst gas-phase thermolysis of a compound of formula (II)

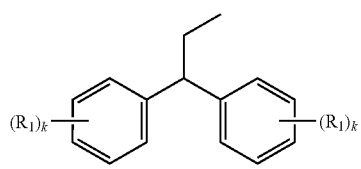
(II)

with respect to the compound of formula (I-a)

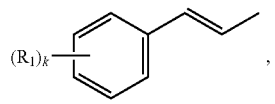
(I-a)

wherein
k is, independently from each other, 0, 1, 2 or 3;
$R_1$ is, independently from each other, hydroxy, $C_1$-$C_6$ alkoxy, di($C_1$-$C_6$-alkyl) aminyl, said method comprising employing, comprised in said catalyst, a boron containing zeolitic material comprising a membered ring (MR) pore system greater than 10 MR, wherein in the boron containing zeolitic material, the molar ratio of silicon, calculated as elemental silicon, relative to boron, calculated as elemental boron, is in the range of from 1:1 to 100:1.

50. The method of embodiment 49, wherein the boron containing zeolitic material comprising a membered ring (MR) pore system greater than 10 MR is as defined in any one of embodiments 2 to 14, preferably as defined in embodiment 6 or 7, more preferably as defined in embodiment 7, more preferably as defined in embodiments 9 and 10 insofar embodiments 9 and 10 is dependent of embodiment 7.

51. The method of embodiment 49 or 50, wherein the compound of formula (II) is

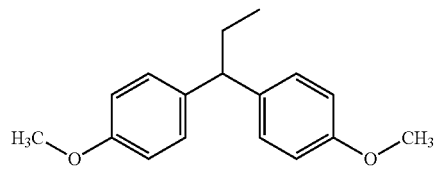
(II)

and the compound of formula (I-a) is

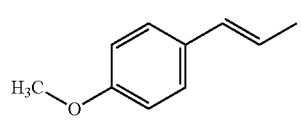
(I-a)

52. Use of a boron containing zeolitic material, preferably a boron containing zeolitic material having framework type MWW, as a catalytic material for preparing a compound of formula (I)

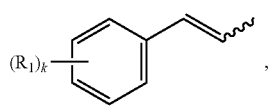
(I)

preferably for increasing the selectivity of solid catalyst gas-phase thermolysis of a compound of formula (II)

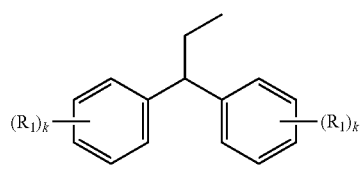
(II)

with respect to the compound of formula (I-a)

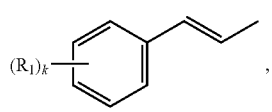
(I-a)

wherein
k is, independently from each other, 0, 1, 2 or 3;
$R_1$ is, independently from each other, hydroxy, $C_1$-$C_6$ alkoxy, di($C_1$-$C_6$-alkyl) aminyl,
wherein the compound of formula (I) is preferably a compound

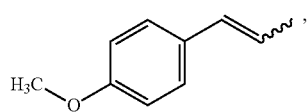

the compound of formula (I-a) is preferably a compound

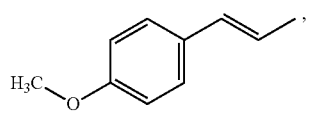

the compound of formula (II) is preferably a compound

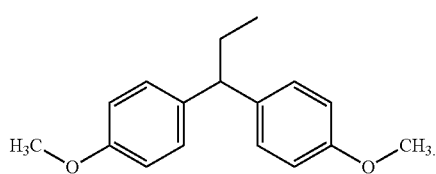

The present invention is further illustrated by the following reference examples, examples and comparative examples.

EXAMPLES

Reference Example 1: Preparation of Zeolitic Materials

Reference Example 1.1: Preparation of a Boron Containing Zeolitic Material Having Framework Type MWW A zeolitic material of framework structure type MWW was prepared according to reference example 1.1 of WO 2013/117536 A. This spray-dried zeolitic material having an MWW framework structure had a boron (B) content of 1.9 wt. %, a silicon (Si) content of 41 wt. %, and a total organic carbon (TOC) content of 0.18 wt. %. 150 g of this calcined spray-dried material and 19.75 g Ludoxe AS-40 and 7.5 g Walocel® (from Wolf Walsrode), together with 158 ml de-ionized water, were mixed in a kneader (koller) for 1 h. The resulting formable mass was extruded to obtain strands having a diameter of 2 mm. The strands were heated with 3 K/min to a 120° C. and dried at this temperature for 12 h under air. Then, the dried strands were heated with 2 K/min to 500° C. and calcined at that temperature for 5 h under air with an air flow of 80 l/h. The resulting catalyst material had a bulk density of 380 g/l.

Reference Example 1.2: Preparation of a Catalyst Comprising a Boron Containing Zeolitic Material Having Framework Type BEA A boron-containing zeolitic material was prepared according to "Example 6", section 6.1, of WO 2013/117537 A. In a kneader, 15 kg of this boron containing zeolitic material were added. To the zeolitic material, 0.45 kg of HNO$_3$ (53 weight-%) dissolved in 2 L de-ionized H$_2$O were added under mixing conditions. The mixture was further mixed for 5 min before 0.75 kg Walocel® were added. The material was further mixed for 5 min before 2 kg of Ludox® AS-40 were admixed with 3 L of de-ionized H$_2$O. After another 5 min of mixing, 6 L of de-ionized H$_2$O are added. After 25 min kneading time, an additional amount of 0.5 L de-ionized H$_2$O were added, followed, after another 15 min of kneading, by 0.2 L de-ionized H$_2$O. The resulting paste was extruded in an extrusion press under a pressure of 120-200 bar. The extrudates (strands having a diameter of 2 mm) were dried in an oven at a temperature of 120° C. for 16 h. The calcination was performed in a convection muffle kiln using the following temperature program: 470 min at 470° C., heating to 500° C. in 15 min and keeping the extrudates at this temperature for 300 min. The final strands had a diameter of 2 mm size. The resulting catalyst material had a bulk density of 523 g/l.

Reference Example 1.3: Preparation of a Catalyst Comprising a Boron Containing Zeolitic Material Having Framework Type ZBM-11

75 kg of a ZBM-11 zeolitic material (a boron containing zeolitic material of mixed framework type MFI and MEL, prepared according example 7 of EP 0 007 081 A, however with a different ratio Si:B) exhibiting a molar ratio of Si relative to B of 18:1 was mixed with 3.75 kg Walocel® (from Wolf Walsrode) in a kneader (koller) for 5 min. Then, 6.0 kg NH$_4$OH was admixed with 12 l de-ionized water, and the mixture was added to the mixture of the zeolitic material and Walocel®. After 10 min, 9.9 Ludox® AS-40 were added and the resulting mixture was kneaded. After 20 min, 44 l de-ionized water were added. After 50 min, Zusoplast 126/3 (from Zschimmer & Schwarz) were added and further 4 l de-ionized water were added. The kneaded mass was subjected to extrusion under 65-80 bar wherein the extruder was cooled with water during the extrusion process. The extrusion time was in the range of from 15 to 20 min. The power consumption during extrusion was 2.4 A. A die head was employed allowing for producing cylindrical strands having a diameter of 2.0 mm. At the die head out outlet, the strands were not subjected to a cutting to length. The strands were dried at a temperature of 150° C. overnight under air. Then, the dried strands were calcined at a temperature of 650° C. under air in a continuous-type with rotary kiln at an air flow of 100 m$^3$/h at a material throughput of about 15 kg/h. The resulting catalyst material had a bulk density of 100 g/l.

Reference Example 1.4: Preparation of a Catalyst Comprising a Zeolitic Material Having Framework Type MWW A zeolitic material of framework structure type MWW was prepared according to example 1.2 of WO 2014/122152 A. This spray-dried zeolitic material having an MWW framework structure had a boron content of 0.08 weight-%, a silicon content of 45 weight-%, a total organic carbon (TOC) content of <0.1 weight-%, and a BET specific surface area determined via nitrogen adsorption at 77 K according to DIN 66131 of 451 m$^2$/g. 3.5 kg of this calcined spray-dried material was kneaded in a kneader (koller) with 0.226 kg Walocel® for 5 min. Then, under kneading conditions, 2.26 kg Ludox® AS-40 were added continuously. After 5 min, the addition of de-ionized water (6.0 l) was started. After further 25 min, 0.6 l de-ionized water were added. After a total kneading time of 45 min, the kneaded mass was extrudable.

The kneaded mass was subjected to extrusion under 65-80 bar wherein the extruder was cooled with water during the extrusion process. The extrusion time was in the range of from 15 to 20 min. The power consumption during extrusion was 2.4 A. A die head was employed allowing for producing cylindrical strands having a diameter of 2.0 mm. At the die head out outlet, the strands were not subjected to a cutting to length. The strands were dried at a temperature of 120° C. for 12 h under air. Then, the dried strands were calcined at a temperature of 500° C. under air for 5 h. The resulting catalyst material had a bulk density of 348 g/l.

Reference Example 1.5: Preparation of a Catalyst Comprising a Zeolitic Material Having Framework Type BEA 300 g of a boron-free H-beta zeolitic material exhibiting a molar ratio of Si relative to Al of 12.5:1 (CP814E from Zeolyst) and 39.47 g Ludox AS-40 and 10.0 g Walocel® (from Wolf Walsrode), were mixed in a kneader (koller) for 10 min. The obtained mass was admixed with 275 ml de-ionized water and kneaded for further 50 min. The resulting formable mass was extruded to obtain strands having a diameter of 2 mm. The strands were heated with 3 K/min to a 120° C. and dried at this temperature for 12 h under air. Then, the dried strands were heated with 2 K/min to 500° C. and calcined at that temperature for 5 h under air with an air flow of 80 l/h. The resulting catalyst material had a bulk density of 420 g/l.

Reference Example 2: Determination of Parameters

Reference Example 2.1: $NH_3$-TPD

The temperature-programmed desorption of ammonia ($NH_3$-TPD) was conducted in an automated chemisorption analysis unit (Micromeritics AutoChem II 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analyzed using the program described below. The temperature was measured by means of a Ni/Cr/Ni thermocouple immediately above the sample in the quartz tube. For the analyses, He of purity 5.0 was used. Before any measurement, a blank sample was analyzed for calibration.
1. Preparation: Commencement of recording; one measurement per second. Wait for 10 minutes at 25° C. and a He flow rate of 30 $cm^3$/min (room temperature (about 25° C.) and 1 atm); heat up to 600° C. at a heating rate of 20 K/min; hold for 10 minutes. Cool down under a He flow (30 $cm^3$/min) to 100° C. at a cooling rate of 20 K/min (furnace ramp temperature); Cool down under a He flow (30 $cm^3$/min) to 100° C. at a cooling rate of 3 K/min (sample ramp temperature).
2. Saturation with $NH_3$: Commencement of recording; one measurement per second. Change the gas flow to a mixture of 10% $NH_3$ in He (75 $cm^3$/min; 100° C. and 1 atm) at 100° C.; hold for 30 minutes.
3. Removal of the excess: Commencement of recording; one measurement per second. Change the gas flow to a He flow of 75 $cm^3$/min (100° C. and 1 atm) at 100° C.; hold for 60 minutes.
4. $NH_3$-TPD: Commencement of recording; one measurement per second. Heat up under a He flow (flow rate: 30 $cm^3$/min) to 600° C. at a heating rate of 10 K/min; hold for 30 minutes.
5. End of measurement.

Desorbed ammonia was measured by means of the online mass spectrometer, which demonstrates that the signal from the thermal conductivity detector was caused by desorbed ammonia. This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

Reference Example 2.2: BET Specific Surface Area

The BET specific surface area values were determined via nitrogen adsorption at 77 K according to DIN 66131.

Example 1: Preparing a Compound of Formula (I) (Anethole) Starting from a Compound of Formula (II) (1,1-bis(4-Methoxyphenyl)Propane)

The first zone (15 cm) of a gas phase oven, equipped with electrical heating means and having an inner diameter of 4 cm, was filled with quartz rings. The downstream zone (20 cm) was then filled with with catalyst strands according to the Reference Examples 1.1 to 1.5. The first 15 cm filled with quartz rings was used as evaporating zone for the dimer and the diluent thereof (water). (The term "dimer" as used in this context refers to a mixture consisting of 70 mol-% 1,1-bis(4-methoxyphenyl)propane, 28 mol-% 1-(4-methoxyphenyl)-1-(2-methoxyphenyl)propane, and 2 mol-% 1,1-bis(2-methoxyphenyl)propane.) Water was introduced into the reactor as diluent. The dimer and the water were introduced into the evaporation zone as separate streams. As carrier gas, technical nitrogen was used at a volume flow of 20 L/h. The thermolytic reaction was carried out at a temperature of the gas phase of 375° C. (B-MWW, B-BEA, ZBM-11) or 350° C. ([ ]-MWW and BEA), and a catalyst loading of 0.2 kg (dimer)/kg (catalyst)/h. The reaction mixture was condensed in a downstream cooling apparatus at a temperature of 5° C. The water was separated by phase separation, and the resulting organic phase was analyzed by gas chromatography.

The results obtained are given in Table 1 below:

TABLE 1

| | | | | | | | |
|---|---|---|---|---|---|---|---|
| Results according to Example 1 | | | | | | | |
| Zeolitic material (ref. ex. #) | Pore system/MR | Molar ratio Si/B | BET specific surface area/$m^2$/g | $NH_3$-TPD/ mmol($NH_3$)/g (zeolitic material) | Conv. dimer [1]/% | Select. (I) [2]/% | Select. (I-a) [3]/% |
| B-MWW (1.1) | 10 + 12 | 14 | 448 | 0.37 | 88.4 | 92.2 | 58.2 |
| B-BEA (1.2) | 12 | 14 | 498 | 0.30 | 68.5 | 79.7 | 59.5 |
| ZBM-11 (1.3) | 10 | 18 | 380 | 0.37 | <20 | 0 | 0 |

TABLE 1-continued

Results according to Example 1

| Zeolitic material (ref. ex. #) | Pore system/MR | Molar ratio Si/B | BET specific surface area/m²/g | NH₃-TPD/ mmol(NH₃)/g (zeolitic material) | Conv. dimer [1]/% | Select. (I) [2]/% | Select. (I-a) [3]/% |
|---|---|---|---|---|---|---|---|
| [ ]-MWW [4] (1.4) | 10 + 12 | >200 | 462 | 0.04 | 0 | 0 | 0 |
| BEA (1.5) | 12 | ∞ | 500 | 1.08 | 68.4 | 74.5 | 53.3 |

[1] Conversion of the dimer (1,1-bis(4-methoxyphenyl)propane plus 1-(4-methoxyphenyl)-1-(2-methoxyphenyl)propane plus 1,1-bis(2-methoxyphenyl)propane).
[2] Selectivity (I) is defined as the sum of the molar amounts of the compounds of formula (I-a) and the para-substituted cis-isomer of formula (I-b), divided by the molar amount of converted dimer (1,1-bis(4-methoxyphenyl)propane plus 1-(4-methoxyphenyl)-1-(2-methoxyphenyl)propane plus 1,1-bis(2-methoxyphenyl)propane).
[3] Selectivity (I-a) is defined as the molar amount of the compound of formula (I-a) divided by the molar amount of converted dimer (1,1-bis(4-methoxyphenyl)propane plus 1-(4-methoxyphenyl)-1-(2-methoxyphenyl)propane plus 1,1-bis(2-methoxyphenyl)propane).
[4] The abbreviation "[ ]-MWW" describes the deboronated zeolite of framework type MWW.

Results

From the examples, it can be seen that a boron containing zeolitic material having a 10 MR pore system (ZBM-11) is not active as a catalyst in the above-discussed reaction whereas a boron containing zeolitic material having a pore system of greater than 10 (B-MWW: 12 MR; B-BEA: 12 MR) is active.

As can be seen from the comparison of a zeolitic material having a 12 MR pore system which, however, does not contain a substantial amount of boron ([ ]-MWW), and the B-MWW material, the presence of a sufficient amount of boron is mandatory to render the zeolitic material having a pore system of greater than 10 MR an active catalyst in the above-discussed reaction.

The influence of boron is also shown by the comparison of a boron-free zeolitic material having a pore system greater than 10 MR (BEA, 12 MR) and the respective boron containing zeolitic material (B-BEA): in particular with respect to the most decisive parameter, the selectivity with regard to the valuable product, an increase from 74.5% to 79.7% could be achieved, i.e. an improvement in selectivity of about 7%.

In particular, it was shown that the yield with regard to the compound of formula (I-a) (in %), calculated as the selectivity (I-a) times the conversion dimer, is very high for B-BEA (41.1%), and even higher for B-MWW.

Cited Prior Art
CN 102491884 A
SU 261380
SU 355144
Maslozhirovaya Promyshlennost (1974), volume 9, pages 29-30
CN 103058835 A
DE 2418974 B1
WO 2013/117536 A
WO 2013/117537 A
WO 2014/122152 A
EP 0 007 081 A

The invention claimed is:

1. A process for preparing a compound of formula (I)

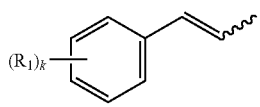

(I)

comprising contacting a compound of formula (II)

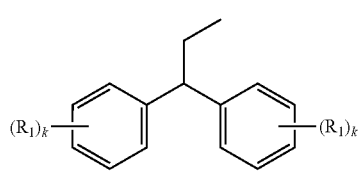

(II)

in the gas phase with a solid catalyst comprising a boron containing zeolitic material comprising a membered ring (MR) pore system greater than 10 MR, wherein k is, independently from each other, 0, 1, 2 or 3;

$R_1$ is, independently from each other, hydroxy, $C_1$-$C_6$ alkoxy, di($C_1$-$C_6$-alkyl) aminyl;

wherein in the boron containing zeolitic material, the molar ratio of silicon, calculated as elemental silicon, relative to boron, calculated as elemental boron, is in the range of from 1:1 to 100:1.

2. The process of claim 1, wherein the boron containing zeolitic material comprises a 12 MR pore system.

3. The process of claim 1, wherein the MR pore system of the boron containing zeolitic material consists of the 12 MR pore system.

4. The process of claim 1, wherein the MR pore system of the boron containing zeolitic material consists of the 12 MR pore system, wherein the boron containing zeolitic material has framework type BEA.

5. The process of claim 1, wherein the boron containing zeolitic material comprises a 12 MR pore system and a 10 MR pore system, wherein the boron containing zeolitic material has framework type MWW.

6. The process of claim 1, wherein the boron containing zeolitic material consists of the 12 MR pore system and the 10 MR pore system, wherein the boron containing zeolitic material has framework type MWW.

7. The process of claim 1, wherein $C_1$-$C_6$ alkoxy is selected from the group consisting of methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy, and wherein in di($C_1$-$C_6$-alkyl) aminyl, the $C_1$-$C_6$-alkyl is selected from the group consisting of methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl and 1-ethyl-2-methylpropyl.

8. The process of claim 1, wherein the compound of formula (I) is a compound of formula

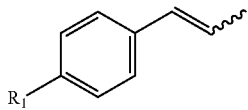
(I)

and the compound of formula (II) is a compound of formula

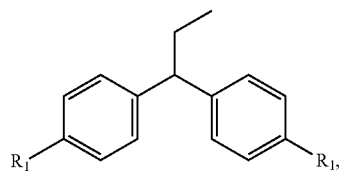
(II)

wherein the compound of formula (I) is a compound of formula

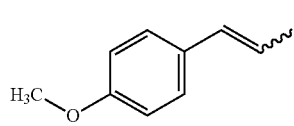
(I)

and the compound of formula (II) is a compound of formula

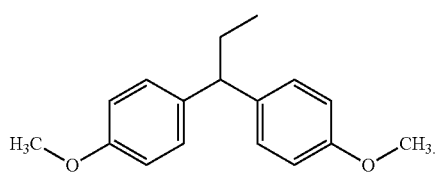
(II)

9. The process of claim 1, wherein in the boron containing zeolitic material, the molar ratio of silicon, calculated as elemental silicon, relative to boron, calculated as elemental boron, is in the range of from 5:1 to 50:1.

10. The process of claim 1, wherein in the boron containing zeolitic material, the molar ratio of silicon, calculated as elemental silicon, relative to boron, calculated as elemental boron, is in the range of from 10:1 to 20:1.

11. The process of claim 1, wherein at least 99 weight % of the boron containing zeolitic material consists of boron, silicon, oxygen, and hydrogen.

12. The process of claim 1, wherein the solid catalyst further comprises a binder material, wherein at least 99.9 weight-% of the binder material consist of silica.

13. The process of claim 1, wherein contacting the compound of formula (II) with the solid catalyst comprising a boron containing zeolitic material is carried out under thermolytic conditions at a temperature of the gas phase in the range of from 250 to 650° C., and at an absolute pressure of the gas phase in the range of from 0.1 to 2.0 bar.

14. The process of claim 1, wherein contacting the compound of formula (II) with the solid catalyst comprising a boron containing zeolitic material is carried out under thermolytic conditions at a temperature of the gas phase in the range of from 300 to 400° C., and at an absolute pressure of the gas phase in the range of from 0.8 to 1.1 bar.

15. The process of claim 1, wherein contacting the compound of formula (II) with the solid catalyst comprising a boron containing zeolitic material is carried out in the presence of a diluent, and wherein the gas phase further comprises a carrier gas.

16. The process of claim 1, wherein contacting the compound of formula (II) with the solid catalyst comprising a boron containing zeolitic material is carried out in continuous mode, at a catalyst load in the range of from 0.01 to 5 kg (compound of formula (II))/kg (catalyst)/h.

17. The process of claim 1, wherein contacting the compound of formula (II) with the solid catalyst comprising a boron containing zeolitic material is carried out in continuous mode, at a catalyst load in the range of from 0.1 to 0.5 kg (compound of formula (II))/kg (catalyst)/h.

18. The process of claim 1, further comprising cooling the reaction mixture, obtained from contacting the compound of formula (II) in the gas phase with the solid catalyst, to a temperature in the range of from 0 to 40° C.

19. The process of claim 1, wherein the compound of formula (I) comprises a compound of formula (I-a)

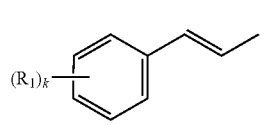
(I-a)

and a compound of formula (I-b)

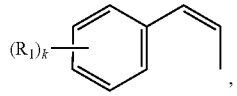
(I-b)

said process further comprising separating the compound of formula (I-a) from the compound of formula (I-b), by distillation.

20. The process of claim 2, wherein the compound of formula (I) comprises a compound of formula (I-a)

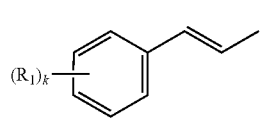
(I-a)

and a compound of formula (I-b)

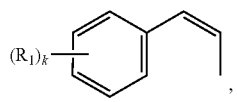
(I-b)

said process further comprising separating the compound of formula (I-a) from the compound of formula (I-b), by distillation.

21. A process for increasing the selectivity of solid catalyst gas-phase thermolysis of a compound of formula (II)

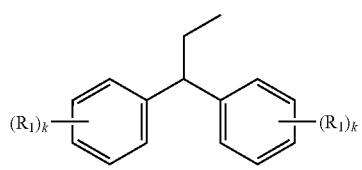

with respect to the compound of formula (I-a)

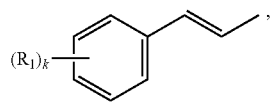

wherein
k is, independently from each other, 0, 1, 2 or 3;
R₁ is, independently from each other, hydroxy, $C_1$-$C_6$ alkoxy, di($C_1$-$C_6$-alkyl) aminyl,
which comprises utilizing a boron containing zeolite material comprising a membered ring (MR) pore system greater than 10 MR, wherein in the boron containing zeolitic material, the molar ratio of silicon, calculated as elemental silicon, relative to boron, calculated as elemental boron, is in the range of from 1:1 to 100:1.

* * * * *